US010404976B2

United States Patent
Jain et al.

(10) Patent No.: US 10,404,976 B2
(45) Date of Patent: Sep. 3, 2019

(54) INTRA-OPERATIVE QUALITY MONITORING OF TRACKING SYSTEMS

(71) Applicant: KONINKLIJKE PHILIPS N.V., Eindhoven (NL)

(72) Inventors: Ameet Kumar Jain, New York, NY (US); Vijay Parthasarathy, Tarrytown, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1013 days.

(21) Appl. No.: 14/364,336

(22) PCT Filed: Dec. 27, 2012

(86) PCT No.: PCT/IB2012/057745
§ 371 (c)(1),
(2) Date: Jun. 11, 2014

(87) PCT Pub. No.: WO2013/098768
PCT Pub. Date: Jul. 4, 2013

(65) Prior Publication Data
US 2014/0375822 A1 Dec. 25, 2014

Related U.S. Application Data

(60) Provisional application No. 61/580,519, filed on Dec. 27, 2011.

(51) Int. Cl.
*A61B 5/06* (2006.01)
*H04N 17/00* (2006.01)
(Continued)

(52) U.S. Cl.
CPC ............ *H04N 17/002* (2013.01); *A61B 5/06* (2013.01); *A61B 6/4417* (2013.01);
(Continued)

(58) Field of Classification Search
CPC ....... A61B 5/06; A61B 8/4254; A61B 8/4416; A61B 2017/00725
(Continued)

(56) References Cited

U.S. PATENT DOCUMENTS 8,165,372 B2   4/2012   Ishikawa et al.
8,204,576 B2   6/2012   Ikuma et al.
(Continued)

FOREIGN PATENT DOCUMENTS

CN   101108140 A   1/2008
DE   102010020781   11/2011
(Continued)

*Primary Examiner* — Peter Luong

(57) ABSTRACT

An interventional system employing an interventional tool (20) having a tracking point, and an imaging system (30) operable for generating at least one image of at least a portion of the interventional tool (20) relative to an anatomical region of a body. The system further employs a tracking system (40) operable for tracking any movements of the interventional tool (20) and the imaging system (30) within a spatial reference frame relative to the anatomical region of the body, wherein the tracking system (40) is calibrated to the interventional tool (20) and the imaging system (30) and a tracking quality monitor (52) operable for monitoring a tracking quality of the tracking system (40) as a function of a calibrated location error for each image between a calibrated tracking location of the tracking point within the spatial reference frame and an image coordinate location of the tracking point in the image.

15 Claims, 5 Drawing Sheets

(51) Int. Cl.
   *A61B 6/00*      (2006.01)
   *A61B 8/00*      (2006.01)
   *A61B 34/20*     (2016.01)
   *G06T 7/80*      (2017.01)
   *A61B 17/00*     (2006.01)
   *A61B 90/00*     (2016.01)

(52) U.S. Cl.
   CPC .......... *A61B 8/4254* (2013.01); *A61B 8/4416* (2013.01); *A61B 34/20* (2016.02); *G06T 7/80* (2017.01); *A61B 5/062* (2013.01); *A61B 2017/00725* (2013.01); *A61B 2090/0818* (2016.02); *A61B 2090/364* (2016.02); *G06T 2207/30004* (2013.01)

(58) Field of Classification Search
   USPC ........................................................ 600/424
   See application file for complete search history.

(56) References Cited

U.S. PATENT DOCUMENTS

| | | |
|---|---|---|
| 8,886,286 B2 | 11/2014 | Graumann et al. |
| 2002/0035321 A1* | 3/2002 | Bucholz ............... A61B 5/0064 600/407 |
| 2004/0002642 A1 | 1/2004 | Dekel et al. |
| 2006/0258938 A1 | 11/2006 | Hoffman et al. |
| 2008/0125997 A1 | 5/2008 | Li et al. |
| 2008/0283771 A1 | 11/2008 | Li |
| 2008/0306379 A1 | 12/2008 | Ikuma et al. |
| 2009/0205403 A1 | 8/2009 | Boese et al. |
| 2009/0306497 A1 | 12/2009 | Manzke et al. |
| 2010/0168556 A1 | 7/2010 | Shen et al. |
| 2010/0239150 A1 | 9/2010 | Ishikawa et al. |
| 2010/0290685 A1 | 11/2010 | Wein et al. |
| 2011/0009740 A1 | 1/2011 | Hauck |
| 2013/0066196 A1* | 3/2013 | Graumann ............... A61B 6/12 600/424 |
| 2014/0375822 A1 | 12/2014 | Jain et al. |

FOREIGN PATENT DOCUMENTS

| | | |
|---|---|---|
| RU | 2422084 C2 | 6/2011 |
| WO | 0101845 A2 | 1/2001 |
| WO | WO2010076676 | 7/2010 |
| WO | WO2010102119 | 9/2010 |

* cited by examiner

INTRA-OPERATIVE QUALITY MONITORING OF TRACKING SYSTEMS

CROSS-REFERENCE TO PRIOR APPLICATIONS

This application is the U.S. National Phase application under 35 U.S.C. § 371 of International Application Serial No. PCT/IB2012/057745, filed on Dec. 27, 2012, which claims the benefit of U.S. Application Ser. No. 61/580,519, filed on Dec. 27, 2011. These applications are hereby incorporated by reference herein.

The present invention generally relates to interventional procedures for a diagnosis and/or a treatment of a body, human or animal, that may involve making a cut or a hole to gain access to the inside of the body, or gaining access to a body cavity without cutting into the body, or administering electromagnetic radiation (e.g., X-rays, lasers, gamma-rays and ultraviolet light) to the body. The present invention specifically relates to an intra-operative quality monitoring of a calibration of a tracking system for an interventional tool during the interventional procedure.

FIG. 1 illustrates a known interventional system employing one or more intervention tools 20, one or more imaging systems 30, a tracking system 40, and a workstation 50.

Each intervention tool 20 may be any type of tool, instrument, device, gadget, etc. structurally configured for performing a specific action during an interventional procedure. Examples of an intervention tool 20 include, but are not limited to, endoscopes, catheters and ultrasound ("US") probes.

Each imaging system 30 may be any type of system structurally configured for generating images of an anatomical region of a body during an interventional procedure. Examples of an imaging system 30 include, but are not limited to, X-ray systems and US systems.

Tracking system 40 may be any type of system structurally configured for tracking movement(s) of intervention tool(s) 20 within a spatial reference frame during the interventional procedure. Examples of tracking system 40 include, but are not limited to, electromagnetic ("EM") tracking systems and optical tracking systems.

Workstation 50 may consist of any type of assembled equipment structurally configured for processing image data 31 from imaging system(s) 30 and tracking data 41 from tracking system 40 to visualize positions of intervention tool(s) 20 within a spatial reference frame relative to registered images of the anatomical region of the body during the interventional procedure. Examples of workstation 50 include, but are not limited to, a computer having an (1) intervention navigator application 51 for processing image data 31 and tracking data 41 to display positions of intervention tool(s) 20 within the spatial reference frame relative to registered images of the anatomical region of the body, and (2) a graphical user interface ("GUI") (not shown) for interacting with intervention navigator application 51.

Of particular importance to any interventional procedure is a calibration of tracking system 40. For example, an EM tracking system typically employs one or more magnetic field sources for defining the spatial reference frame and one or more magnetic sensors for measuring the fields produced by the magnetic field sources whereby the measurements are utilized to determine the position(s) of intervention tool(s) 20 within the spatial reference frame. This technique relies on accurate prior knowledge of the relative positions of the sources and the spatial forms of their magnetic fields, and of the relative positions and sensitivities of the magnetic sensors. Because it is not possible to manufacture magnetic sources and magnetic sensors with ideal characteristics, purely theoretical calculations of such characteristics are likely to be erroneous and hence they must be determined from calibration measurements prior to or during the interventional procedure. The calibration of the EM tracking system ensures an accurate registration of images generated by imaging system(s) 30 (e.g., an X-ray imaging system and/or a US imaging system).

However, the registration of the images generated by imaging system(s) 30 may nonetheless become erroneous during the interventional procedure due to a variety of reasons including, but not limited to, calibration errors, inoperable or malfunctioning magnetic sources/sensors, electromagnetic distortion or interference, motion of a patient table and/or bending of the patient table. To address this potential calibration problem, the present invention provides a tracking quality monitor 52 for workstation 50 as shown in FIG. 2 for monitoring the tracking quality of the calibrated tracking system 40. Specifically, tracking quality monitor 52 implements methods for determining location error(s) of the intervention tool(s) 20 within the spatial reference frame defined by tracking system 40 and for providing alerts and/or corrections of such location error(s).

One form of the present invention is an interventional system employing an interventional tool having a tracking point, an imaging system, a tracking system and a tracking quality monitor. In operation, the imaging system is operable to generate one or more images of a portion or an entirety of the interventional tool relative to an anatomical region of a body. The tracking system tracks any movements of the interventional tool and the imaging system within a spatial reference frame relative to the anatomical region of the body, wherein the tracking system is calibrated to the interventional tool and the imaging system. The tracking quality monitor monitors a tracking quality of the tracking systems as a function of a calibrated location error for each image between a calibrated tracking location of the tracking point within the spatial reference frame and an image coordinate location of the tracking point in the image.

A second form of the present invention is an interventional workstation employing an intervention navigator and a tracking quality monitor. In operation, the intervention navigator visualizes positions of an interventional tool within a spatial reference frame relative to one or more registered images of an anatomical region of a body during an interventional procedure. The tracking quality monitor monitors a tracking quality of the registered images as a function of a calibrated location error for each registered image between a calibrated tracking location of the tracking point within the spatial reference frame and an image coordinate location of the tracking point in the registered image.

A third form of the present invention is an interventional method involving a navigation of an interventional tool relative to an anatomical region of a body, the interventional tool having a tracking point, an operation of an imaging system for generating at least one image of at least a portion of the interventional tool relative to an anatomical region of a body, an operation of a tracking system for tracking any movements of the interventional tool and the imaging system within a spatial reference frame relative to the anatomical region of the body, wherein the tracking system is calibrated to the interventional tool and the imaging system, and a monitoring of a tracking quality of the tracking systems as a function of a calibrated location error for each image between a calibrated tracking location of the tracking point within the spatial reference frame and an image coordinate location of the tracking point in the image.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
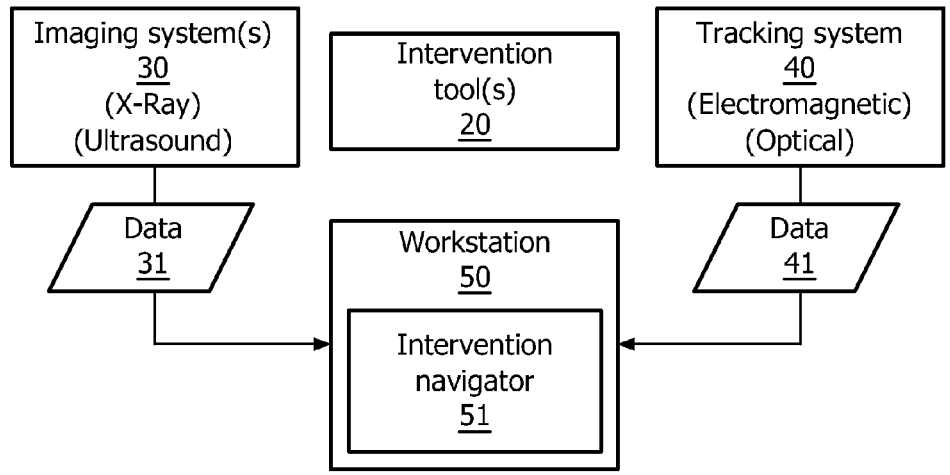
FIG. 1 illustrates an exemplary embodiment of an interventional system as known in the art.
Figure 2:
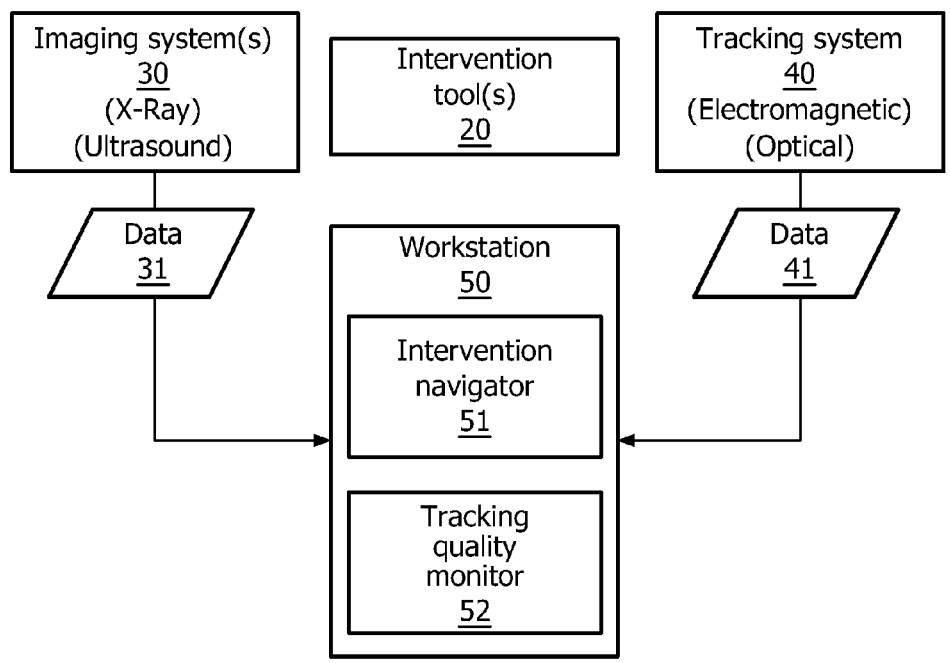
FIG. 2 illustrates an exemplary embodiment of an interventional system in accordance with the present invention.
Figure 3:
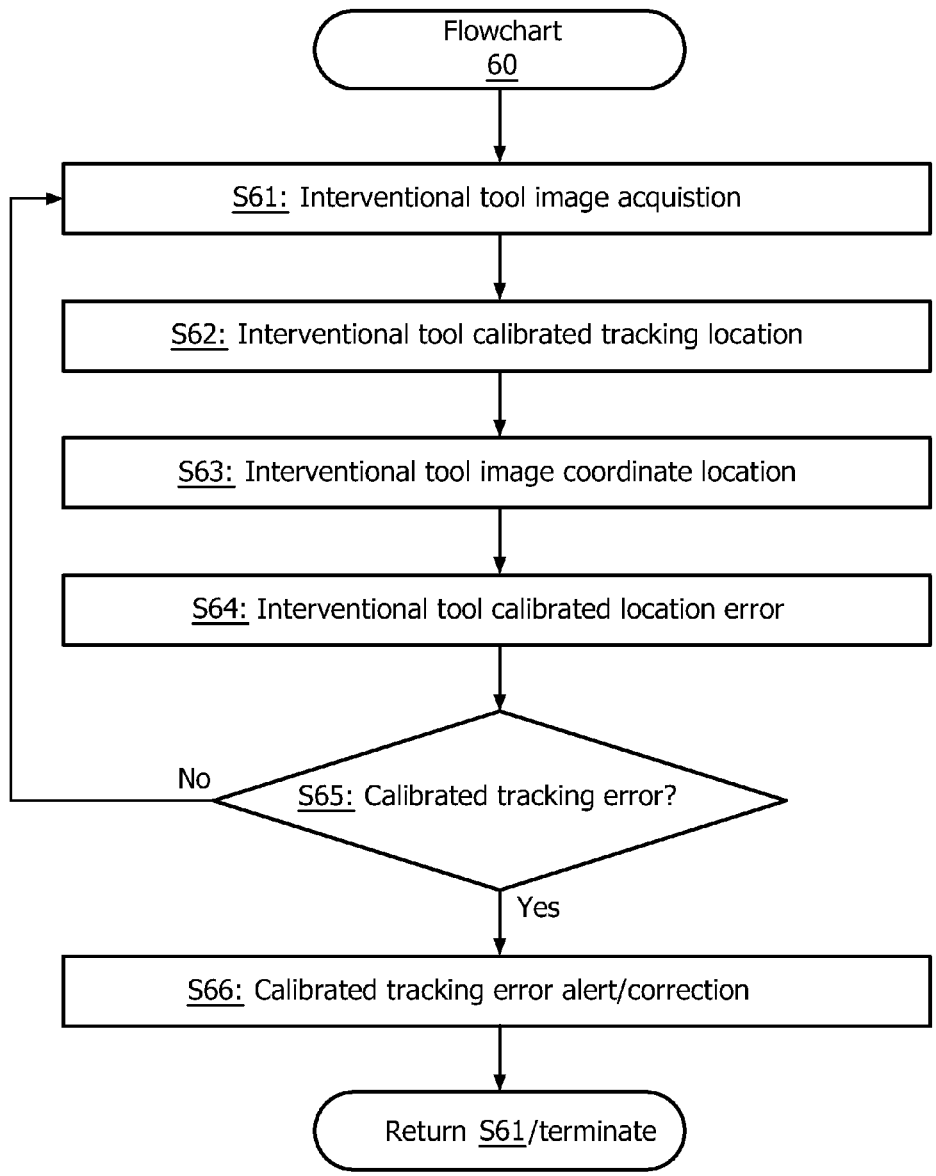
FIG. 3 illustrates a flowchart representative of an exemplary embodiment of a tracking quality monitoring method in accordance with the present invention.

As previously stated herein, tracking quality monitor 52 as shown in FIG. 2 implements methods for determining location error(s) of intervention tool(s) 20 within a spatial reference frame defined by tracking system 40 and for providing alerts and/or corrections of such location error(s). To this end, tracking quality monitor 52 executes flowchart 60 shown in FIG. 3 that is representative of the tracking quality monitoring methods of the present invention.

In general, a stage S61 of flowchart 60 encompasses tracking quality monitor 52 acquiring an image of a portion or an entirely of an interventional tool 20 relative the subject anatomical region of the body (e.g., an X-ray image of a US probe scanning the anatomical region of the body and a US image of the anatomical region of the body).

A stage S62 of flowchart 60 encompasses tracking quality monitor 52 identifying a calibrated tracking location of a tracking point of the interventional tool 20 within the spatial reference frame as tracked by the tracking system 40 (e.g., calibrated tracking location of a tip of a catheter or a head of a US probe within spatial reference frame).

A stage S63 of flowchart 60 encompasses tracking quality monitor 52 identifying an image coordinate location of a tracking point of the interventional tool 20 within the acquired image (e.g., image coordinate location of a tip of a catheter or a head of a US probe within the acquired image). In one embodiment, the identified image coordinate location of the interventional tool 20 is derived from known image segmenting techniques.

A stage S64 of flowchart 60 encompasses tracking quality monitor 52 calculating a calibrated location error of the tracking point of interventional tool 20 between the calibrated tracking location of the interventional tool 20 within the spatial reference frame and the image coordinate location of the tracking point of the interventional tool 20 within the acquired image. In one embodiment, the calibrated location error of the interventional tool 20 is a spatial differential in one or more dimensions of the spatial reference frame between the calibrated tracking location of the tracking point of the interventional tool 20 within the spatial reference frame and the image coordinate location of the tracking point of the interventional tool 20 within the acquired image.

A stage S65 of flowchart 60 encompasses tracking quality monitor 52 determining whether the calibrated location error of the interventional tool 20 represents a calibration tracking error of the interventional tool 20. In one embodiment, tracking quality monitor determines the calibration location error of the interventional tool 20 represents a calibration tracking error of the interventional tool 20 responsive to the calibration location error equaling and/or exceeding a calibration error threshold.

If tracking quality monitor 52 determines the calibrated location error of the interventional tool 20 does not represent a calibration tracking error of the interventional tool 20, then tracking quality monitor 52 returns to stage S61 to acquire any subsequent image of the interventional tool 20 relative the subject anatomical region of the body.

If tracking quality monitor 52 determines the calibrated location error of the interventional tool 20 represents a calibration tracking error of the interventional tool 20, then tracking quality monitor 52 proceeds to a stage S66 of flowchart 60 to provide an alert of the calibrated tracking error and/or to correct the calibrated tracking error. In practice, any alert of the calibrated tracking error may be a visual and/or audio alert, and may occur after the detection on multiple calibration tracking errors. Also, in practice, any correction of the calibrated tracking error may be automatic or semi-automatic and may occur after the detection of multiple calibration tracking errors.

Upon completion of stage S66, tracking quality monitor 52 may return to stage S61 to acquire any subsequent image of the interventional tool 20 relative the subject anatomical region of the body or terminate flowchart 60.

In practice, tracking quality monitor 52 may be utilized for any type of interventional procedure as a quality measure of a calibration of tracking system 40. Nonetheless, to facilitate an understanding of the tracking quality monitoring methods of the present invention, an execution of flowchart 60 by tracking quality monitor 52 will now be described in the context of (1) an X-ray/ultrasound fusion in a cardiac interventional procedure, (2) an ultrasound guided cardiac interventional procedure and (3) an X-ray/electromagnetic calibration for a cardiac interventional procedure.

X-ray/Ultrasound Fusion in a Cardiac Interventional Procedure.

Figure 4:
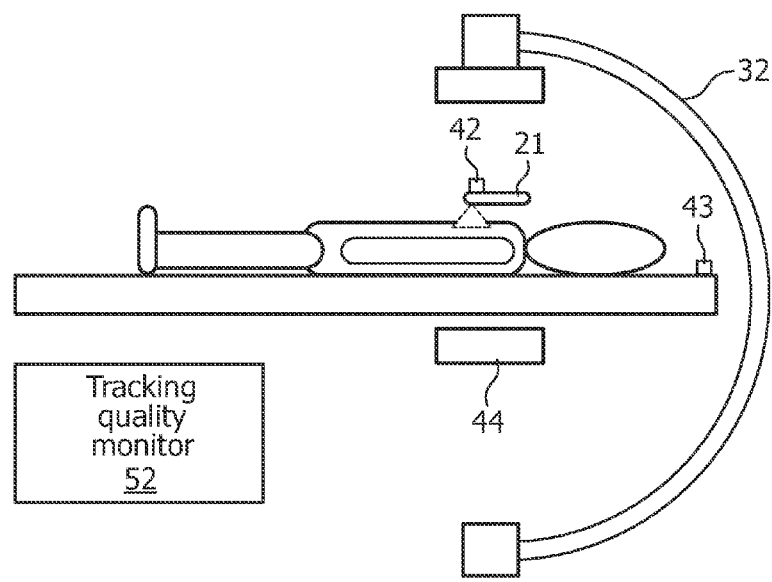
FIG. 4 illustrates a first exemplary interventional implementation of the flowchart shown in FIG. 3.

Techniques for improved heart visualization for advanced cardiac interventions under X-ray guidance are constantly being investigated. One example for improved soft-tissue visualization has been the fusion of live two-dimensional ("2D")/three-dimensional ("3D") US imaging on streaming X-ray imaging using EM tracking. For example, FIG. 4 illustrates an interventional procedure involving a registration of an US probe 21 (e.g., a trans esophageal probe) and an X-ray imager 32. An EM sensor 42 is affixed to US probe 21 and pre-calibrated to the 2D/3D US image, and an EM sensor 43 is affixed to a patient table and pre-calibrated to X-ray imager 32 whereby a real-time stream of X-ray images are permanently registered to the US images. An EM source 44 is operated for purposes of tracking EM sensors 42 and 43 within a spatial reference frame defined by EM source 44. The challenge is the US/X-ray registration may become erroneous due to a variety of reasons, which would result in a decrease in the accuracy and reliability of the interventional procedure.

To address the potential erroneous US/X-ray registration, tracking quality monitor 52 (FIG. 2) continuously runs in the background and monitors the health of the registration as the procedure proceeds regularly. Generally, every time an X-ray image is shot by a clinician as part of the regular clinical protocol, tracking quality monitor 52 identifies an image coordinate location of a head of the US probe 21 on the X-ray image and compares the image coordinate location of the head of US probe 21 to an expected calibration tracking location of the tip of US probe 21 on the X-ray image via the current US/X-ray registration. Tracking quality monitor 52 continually computes any calibrated location error of the head of US probe 21, makes a log of the calibrated location errors, and alerts the clinician if a significant error drift is detected in the calibration location errors (i.e., a calibration location errors equals and/or exceeds a calibration error threshold).

In the context of flowchart 30 (FIG. 3), stage S61 of flowchart 60 encompasses tracking quality monitor 52 acquiring and storing each X-ray image of the cardiac region of the patient. Alternatively, tracking quality monitor 52 acquires and stores every nth X-ray image taken of the cardiac region of the patient, where n•2.

Figures 5A, 5B:
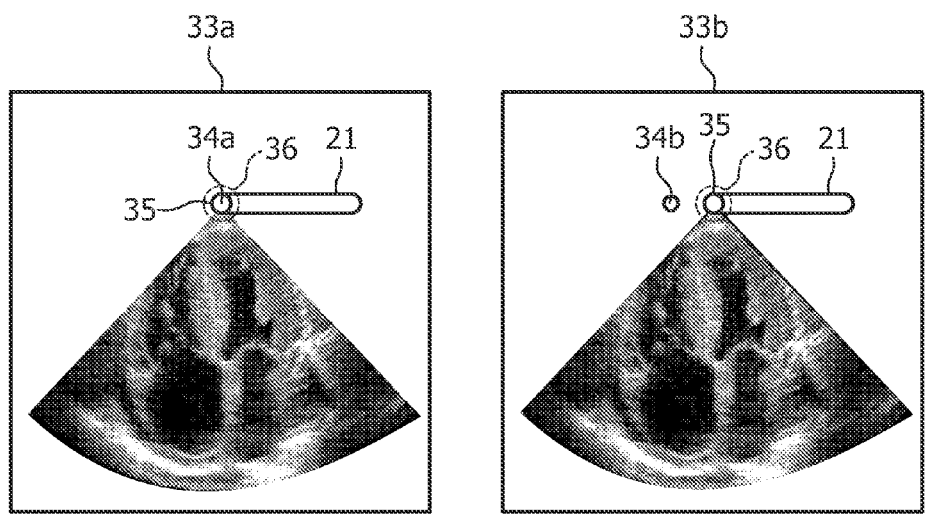
FIG. 5 illustrates an exemplary tracking quality monitoring of the interventional implementation shown in FIG. 4.

Upon an acquisition and storage of an X-ray image, stage S62 of flowchart 60 encompasses tracking quality monitor 52 computing a calibrated tracking location of the head of US probe 21 within the X-ray image using the known US/X-ray registration matrix and stage S63 of flowchart 60 encompasses tracking quality monitor 52 computing an image coordinate location of the head of US probe 21 within the X-ray image using known segmentation algorithms for segmenting the head of US probe 21 or for extracting an approximate six (6) degrees-of-freedom ("DOF") pose of US probe 21. For example, FIG. 5A shows a calibrated tracking location 34*a* and an image coordinate location 35 of the head of US probe 21 within X-ray image 33*a*, and FIG. 5B shows a calibrated tracking location 34*b* and an image coordinate location 35 of the head of US probe 21 within X-ray image 33*b*. Please note the remaining portions of X-ray images 33 is omitted for clarity of locations 34 and 35.

Stage S64 of flowchart 60 encompasses tracking quality monitor 52 comparing the calibrated tracking location of the head of US probe 21 within the X-ray image to the image coordinate location of the head of US probe 21 within the X-ray image to determine and log a calibration tracking between the two (2) locations. The comparison indicates an acceptable US/X-ray image registration during a stage S65 of flowchart 60 if the calibration tracking is less than or equal to a maximum allowable calibration error threshold encircling the image coordinate location. For example, FIG. 5A shows calibrated tracking location 34*a* matching image coordinate location 35 within a calibration tracking threshold 36 and thus an acceptable US/X-ray image registration has been determined by tracking quality monitor 52. If the comparison indicates an acceptable US/X-ray image registration, then tracking quality monitor 52 returns to stage S61 to acquire and store another X-ray image.

Conversely, the comparison indicates an unacceptable US/X-ray image registration during stage S65 of flowchart 60 if the calibration tracking exceeds the maximum allowable calibration tracking threshold encircling the image coordinate location. For example, FIG. 5B shows calibrated tracking location 34*b* being outside of calibration tracking threshold 36 and thus an unacceptable US/X-ray image registration has been determined by tracking quality monitor 52. If the comparison indicates an unacceptable US/X-ray image registration, then tracking quality monitor 52 proceeds to a stage S66 of flowchart 60 to provide a tracking alert and/or to implement a correction to the US/X-ray image registration as needed.

For the tracking alert, tracking quality monitor 52 may alert a clinician to review the log of calibration tracking errors to ascertain whether or not to proceed with the interventional procedure and/or to request a correction to the unacceptable registration.

For an automatic or semi-automatic registration correction, tracking quality monitor 52 may optimize the appropriate registration matrix to get matched up correctly. Such optimization must be performed over multiple X-ray images for stable results and will need X-ray images from two different angles. More particularly, if multiple X-ray images are obtained, as and when they are captured, then all of the X-ray images may be used together to make a statistically strong estimate. Also note that these X-ray images may be captured as part of regular clinical workflow, or intentionally captured for the purpose of correction.

It may be observed that due to the nature of projective geometry, uncertainty of a calibration tracking error in the depth direction of a particular X-ray image will be much higher than the direction parallel to the X-ray image. However, a processing of a second oblique X-ray image may resolve this issue.

Furthermore, cumulative error information may be used to breakdown the error into both a first error due to changes in the registration and a second error due to random events (e.g., EM distortion and C-arm tracking errors).

Ultrasound Guidance in a Cardiac Interventional Procedure.

Figure 6:
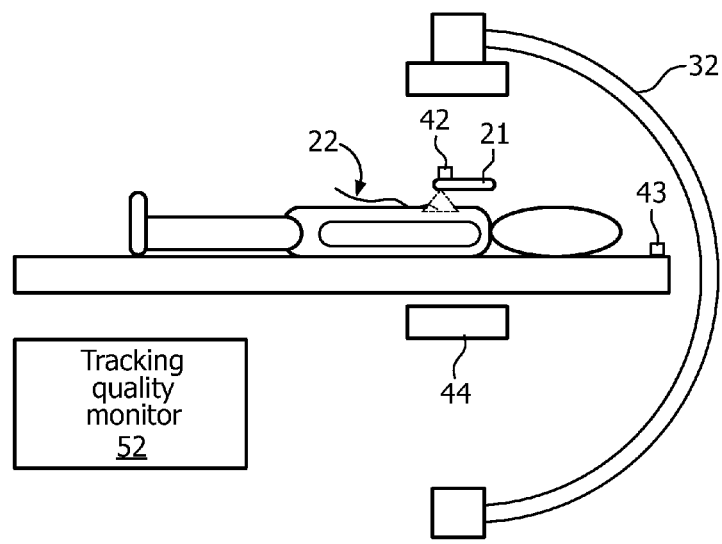
FIG. 6 illustrates a second exemplary interventional implementation of the flowchart shown in FIG. 3.

Another example for improved soft-tissue visualization has been the fusion of live 2D/3D US on streaming X-ray, together with a tracked catheter, using EM tracking. For example, FIG. 6 illustrates an interventional procedure of FIG. 4 with the addition of a tracked catheter 22. Again, the challenge is the US/X-ray registration may become erroneous due to a variety of reasons, which would result in a decrease in the accuracy and reliability of the interventional procedure.

To address the potential erroneous US/X-ray registration, tracking quality monitor 52 (FIG. 2) continuously runs in the background and updates the EM tracking errors inside the beating heart. Generally, tracking quality monitor 52 utilizes a live segmentation of the tip of catheter 22 as known in the art and the corresponding EM tracked position of the tip of catheter 22. Once a sufficient number of such data-points are collected, tracking quality monitor 52 runs an algorithm to determine the most likely error distribution to fit this data. This live error-map inside the heart may be displayed to the clinician. Furthermore, the map may be used for automatically notifying the clinician when the error goes out of bound. This will significantly increase the confidence and accuracy of the system.

In the context of flowchart 60 (FIG. 3), stage S61 of flowchart 60 encompasses tracking quality monitor 52 acquiring and storing each US image of the cardiac region of the patient. Alternatively, tracking quality monitor 52 acquires and stores every nth US image taken of the cardiac region of the patient, where n•2.

Figures 7, 8:
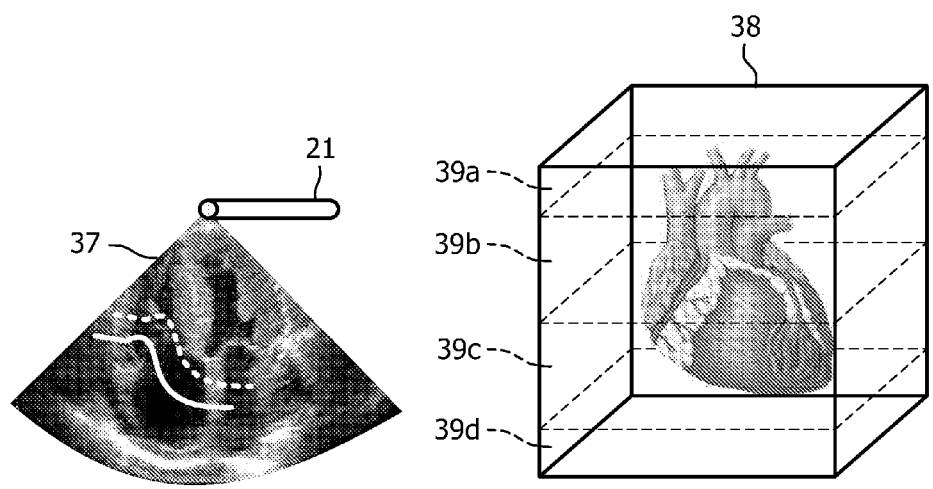
FIGS. 7 and 8 illustrate an exemplary tracking quality monitoring of the interventional implementation shown in FIG. 6.

Upon an acquisition and storage of the US image, a stage S62 of flowchart 60 encompasses tracking quality monitor 52 computing a calibrated tracking location of a tip of catheter 22 within the US image using the known US/X-ray registration matrix and a stage S63 of flowchart 60 encompasses tracking quality monitor 52 computing an image coordinate location of the tip of catheter 22 within the US image using known segmentation algorithms for segmenting the tip of catheter 22. For example, FIG. 7 shows a calibrated tracking location of catheter 22 represented by the dashed white line within a US image 37 and an image coordinate location 35 of catheter 22 represented by the sold white line within US image 37.

In practice, not all US images will be of sufficient quality to allow for segmentation. Typically, US images stream at 30 volume/second. As such, a good segmentation may be achieved every 10-1000 volumes of the US images.

Stage S64 of flowchart 60 encompasses tracking quality monitor 52 comparing the calibrated tracking location of the tip of catheter 22 within the US image to the image coordinate location of the tip of catheter 22 within the US image to determine and log a calibration tracking between the two (2) locations.

In a base embodiment of stage S64, the comparison indicates an acceptable registration during a stage S65 of flowchart 60 if the calibration location error is less than or equal to a maximum allowable calibration tracking threshold encircling the image coordinate location. If the comparison indicates an acceptable registration, then tracking quality monitor 52 returns to stage S61 of flowchart 60 to acquire and store another US image.

Conversely, the comparison indicates an unacceptable registration during stage S65 of flowchart 60 if the calibration location error exceeds the maximum allowable calibration tracking threshold encircling the image coordinate location. If the comparison indicates an unacceptable registration, then tracking quality monitor 52 proceeds to a stage S66 of flowchart 60 to provide a tracking alert and/or to implement a correction to the registration as needed.

Due to uncertainties in US segmentation, the base embodiment of stage S64 may not provide a good estimate of the EM tracking error at the location. Furthermore, errors in EM tracking of catheter 22 will be mixed with errors in US-EM calibration. As such, a mapping embodiment of stage S64 encompasses tracking quality monitor 52 collecting multiple error datasets for making a statistically relevant map. Specifically, for all the captured and relevant volumes, the EM position, the segmented position, and segmentation confidence values are fed to a known algorithm. The algorithm runs a statistical optimization method to compute a 3D map of the EM error distribution inside the 3D volume, such as, for example, a 3D map 38 shown in FIG. 8 having different error zones 39a-39d. The algorithm interpolates to make this error distribution smooth within the 3D map and outputs any systematic errors it finds in the US-EM calibration. When the algorithm computes such an offset, the algorithm will also measure the confidence of such an offset.

Furthermore, the algorithm may use for 'initialization' pre-computed EM error maps from previous experiments. Especially since the error maps computation is not rightly conditioned, the probabilistic estimate will gain significantly with an error map that the system expects. These pre-computed maps may also give qualitative information like the isotropy (equal/unequal) distribution of errors in various dimensions.

The mapping embodiment of stage S64 may also incorporate imaging data from X-ray imager 32. The challenge however will be to integrate it correctly. For example, the segmentation uncertainties in X-ray image are probably lower in the plane of the image. However, the uncertainty in the depth is unknown/higher. A probabilistic approach will help in significantly improving this estimate. Note that if multiple X-ray images are obtained, as and when they are captured, they can all be used together to make a statistically strong estimate. Also, note that these X-ray images may be captured as part of regular clinical workflow, or intentionally captured for the purpose of correction.

Using this error map during stage S65, tracking quality monitor 52 may automatically judge the accuracy of the EM tracking of catheter 22 and store that value in a log. If the calibration location error is less than or equal to a calibration error threshold, tracking quality monitor 52 returns to stage S61 to acquire and store another US image and/or X-ray image. If the calibration location error exceeds the calibration error threshold, tracking quality monitor 52 to stage S66 of flowchart 60 to provide a tracking alert and/or to implement a correction to the registration as needed.

For flowchart 60, once one particular error map is computed, tracking quality monitor 52 updates the error map as each new US image is acquired and stored. As a new data point (EM position, image segmentation, and confidence) becomes available, the error map is updated on the fly by tracking quality monitor 52. If new updates to the map are sudden and inconsistent, a warning may be raised to the clinician.

For the tracking alert of stage S66, tracking quality monitor 52 may alert a clinician to review the log of calibration error trackings to ascertain whether or not to proceed with the interventional procedure and/or to request a correction to the unacceptable registration.

For an automatic or semi-automatic registration correction of stage S66, tracking quality monitor 52 may optimize the appropriate registration matrix to get matched up correctly. Such optimization must be performed over multiple US images (and/or X-ray images) for stable results and will need US images (and/or X-ray images) from two different angles. More particularly, if multiple US images (and/or X-ray images) are obtained, as and when they are captured, then all of the US images (and/or X-ray images) be used together to make a statistically strong estimate. Also note that these US images (and/or X-ray images) may be captured as part of regular clinical workflow, or intentionally captured for the purpose of correction.

X-Ray Guidance in a Cardiac Interventional Procedure.

Figure 9:
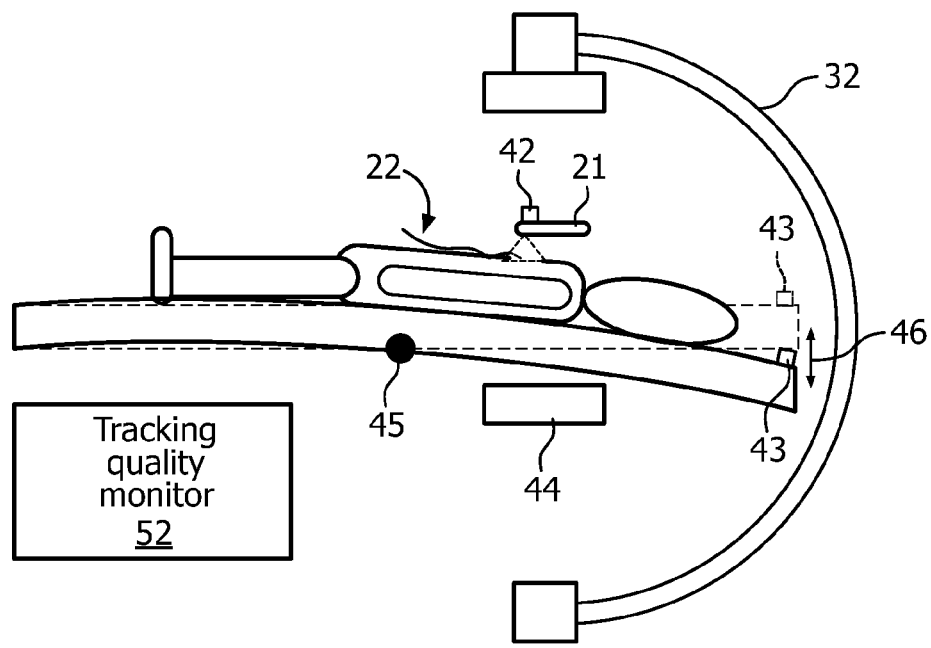
FIG. 9 illustrates a third exemplary interventional implementation of the flowchart shown in FIG. 3.

A currently popular method is to overlay a virtual location of a catheter on X-ray using EM tracking. For example, FIG. 9 shows an X-ray imager 32 pre-calibrated to an EM tracking system by attaching a reference sensor 43 to a patient table. This X-ray/EM calibration drifts over time decreasing the accuracy of the overlay. The primary reason is table bending (~5-10 mm) due to varying patient weights. For example, FIG. 9 shows an exaggerated bending of the patient table with a displacement 46 in a vertical direction and rotation relative to horizontal axis 45.

To address this drift, tracking quality monitor 52 intra-operatively monitors and corrects this registration by comparing the actual X-ray image of catheter 22 to that estimated from the intrinsic pre-calibration. Generally, tracking quality monitor 52 continuously runs in the background as an optimization, and monitors to health of the registration as the interventional procedure proceeds regularly. Every time an X-ray image is shot by the clinician as part of the regular clinical protocol, tracking quality monitor 52 computes the table bending and corrects the calibration (if needed). Tracking quality monitor 52 may compute both the intra-operative correction and visualize errors from other random sources.

In the context of flowchart 60 (FIG. 3), stage S61 of flowchart 60 encompasses tracking quality monitor 52 acquiring and storing each X-ray image of the cardiac region of the patient. Alternatively, tracking quality monitor 52 acquires and stores every nth X-ray image taken of the cardiac region of the patient, where n•2.

Figure 10:
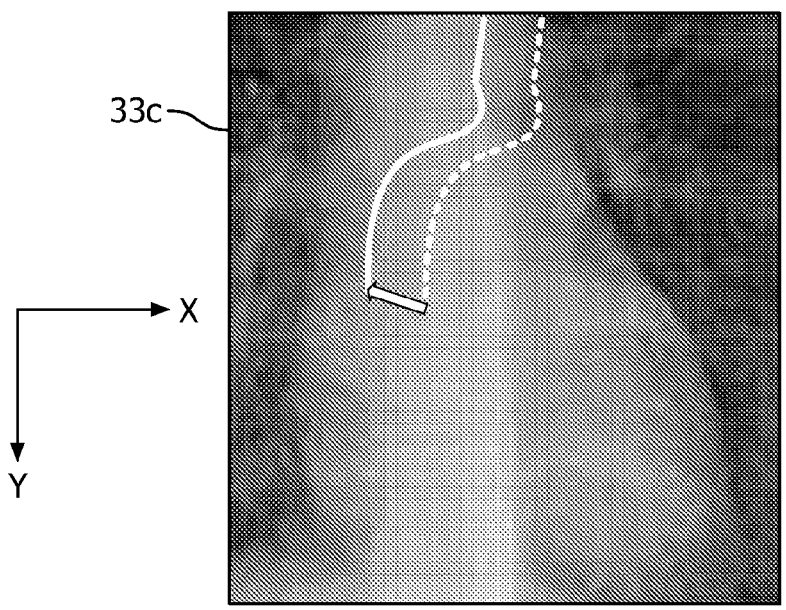
FIG. 10 illustrates an exemplary tracking quality monitoring of the interventional implementation shown in FIG. 9.

Upon an acquisition and storage of the X-ray image, stage S62 of flowchart 60 encompasses tracking quality monitor 52 computing a calibrated tracking location of a tip of catheter 22 within the X-ray image using the known EM/X-ray registration matrix and stage S63 of flowchart 60 encompasses tracking quality monitor 52 computing an image coordinate location of the tip of catheter 22 within the X-ray image using known segmentation algorithms for segmenting the tip of catheter 22. For example, FIG. 10 shows a calibrated tracking location of catheter 22 represented by the dashed white line within a X-ray image 70 and image coordinate location 35 of catheter 22 represented by the sold white line within X-ray image 33c.

Stage S64 of flowchart 60 encompasses tracking quality monitor 52 comparing the calibrated tracking location of the tip of catheter 22 within the X-ray image to the image coordinate location of the tip of catheter 22 within the X-ray image to determine and log an error between the two (2) locations. For example, FIG. 10 shows an error in the form of a white vector pointing from the calibrated tracking location to the image coordinate location.

For this error, an X-error depends on the C-arm rotation, a Y-error depends on the bending of the patient table and the remaining error is random. The table motion may be estimated from error vector and continuously refined during the cardiac interventional procedure.

More particularly, using this error, tracking quality monitor 52 optimizes the table parameters during stage S66. Also, observed that due to the special bending of the table, a typical X-ray image in the AP orientation will not experience as much visualization error, as an image in an oblique orientation. This cumulative error information may be used to breakdown the error into both error due to changes in the calibration, and that from random events (like EM distortion and C-arm tracking errors). Hence tracking quality monitor 52 corrects for systematic errors from the calibration and estimates the amount of extraneous errors (primarily tracking). This tracking error may be presented as the residual error left in the system after the error from the updated calibration is subtracted.

From the description of FIGS. 1-10 herein, those having ordinary skill in the art will appreciate the numerous benefits of the present invention including, but not limited to, an application of a tracking quality monitor of the present invention to any type of interventional procedure employing a tracking system.

In practice, intervention navigator 51 (FIGS. 1 and 2) and tracking quality monitor 52 (FIG. 2) may be modules consisting of hardware, software and/or firmware as would be appreciated by one skilled in the art of the present invention. Furthermore, tracking quality monitor 52 may be a component of intervention navigator 51.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. An interventional system, comprising:
   an interventional tool having a tracking point;
   an imaging system operable for generating at least one image of at least a portion of the interventional tool relative to an anatomical region of a body;
   a tracking system operable for tracking any movements of the interventional tool and the imaging system within a spatial reference frame relative to the anatomical region of the body, wherein the tracking system is calibrated to the interventional tool and the imaging system; and
   an interventional workstation in communication with the imaging system and the tracking system,
      wherein the interventional workstation includes a tracking quality monitor operable for monitoring a tracking quality of the tracking system as a function of a calibrated location error for each image between a calibrated tracking location of the tracking point within the spatial reference frame and an image coordinate location of the tracking point in the image.

2. The interventional system of claim 1, wherein each calibration location error is a spatial differential in one or more dimensions of the spatial reference frame between the calibrated tracking location of the tracking point within the spatial reference frame and the image coordinate location of the tracking point in the image.

3. The interventional system of claim 1, wherein the tracking quality monitor is further operable for generating a distribution map of calibration location errors within the spatial reference frame relative to the anatomical region of the body.

4. The interventional system of claim 1, wherein the tracking quality monitor is further operable for providing an alert responsive to at least one calibration location error exceeding a calibrated error threshold.

5. The interventional system of claim 1, wherein the tracking quality monitor is further operable for correcting the calibration of the tracking system to the interventional tool and the imaging system responsive to at least one calibration location error exceeding a calibrated error threshold.

6. The interventional system of claim 1, wherein the interventional tool is an ultrasound probe and the tracking point is a head of the ultrasound probe.

7. The interventional system of claim 1, wherein the interventional tool is a catheter and the tracking point is a tip of the catheter.

8. The interventional system of claim 1, wherein the imaging system is an ultrasound imaging system.

9. The interventional system of claim 1, wherein the imaging system is an X-ray imaging system.

10. The interventional system of claim 1, wherein the tracking system is an electromagnetic tracking system.

11. The interventional system of claim 1, wherein the imaging system is an optical tracking system.

12. An interventional workstation, comprising:
    an intervention navigator operable for visualizing positions of an interventional tool within a spatial reference frame relative to at least one registered image of an anatomical region of a body during an interventional procedure; and
    a tracking quality monitor operable for monitoring a tracking quality of the at least one registered image as a function of a calibrated location error for each registered image between a calibrated tracking location of the tracking point within the spatial reference frame and an image coordinate location of the tracking point in the registered image.

13. The interventional workstation of claim 12, wherein each calibration location error is a spatial differential in one or more dimensions of the spatial reference frame between the calibrated tracking location of the tracking point within the spatial reference frame and the image coordinate location of the tracking point in the image.

14. The interventional workstation of claim 12, wherein the tracking quality monitor is further operable for generating a distribution map of calibration location errors within the spatial reference frame relative to the anatomical region of the body.

15. The interventional workstation of claim 12, wherein the tracking quality monitor is further operable for at least one of providing an alert responsive to at least one calibration location error exceeding a calibrated error threshold and correcting the calibration of the tracking system to the interventional tool and the imaging system responsive to at least one calibration location error exceeding a calibrated error threshold.

* * * * *